United States Patent
Ramon Real et al.

(10) Patent No.: US 11,399,560 B2
(45) Date of Patent: Aug. 2, 2022

(54) CAPSULES CONTAINING TWO PHASES AND METHOD FOR THEIR PREPARATION

(71) Applicant: CAVIAROLI, S.L., Esparreguera (ES)

(72) Inventors: Ramon Ramon Real, Matadepera (ES); Ramon Maria Ramon Ferres, Esparreguera (ES)

(73) Assignee: CAVIAROLI, S.L., Esparreguera (ES)

( * ) Notice: Subject to any disclaimer, the term of this patent is extended or adjusted under 35 U.S.C. 154(b) by 354 days.

(21) Appl. No.: 15/577,296

(22) PCT Filed: Mar. 14, 2016

(86) PCT No.: PCT/ES2016/070160
§ 371 (c)(1),
(2) Date: Nov. 27, 2017

(87) PCT Pub. No.: WO2016/189171
PCT Pub. Date: Dec. 1, 2016

(65) Prior Publication Data
US 2018/0146704 A1 May 31, 2018

(30) Foreign Application Priority Data
May 27, 2015 (ES) .................. ES201530738

(51) Int. Cl.
| | | |
|---|---|---|
| *A23P 10/30* | (2016.01) | |
| *A23D 9/007* | (2006.01) | |
| *A23D 9/04* | (2006.01) | |
| *A23L 27/00* | (2016.01) | |
| *A23G 3/54* | (2006.01) | |
| *A61K 9/16* | (2006.01) | |
| *A23L 27/60* | (2016.01) | |
| *A23L 29/256* | (2016.01) | |
| *A23L 27/50* | (2016.01) | |
| *A23P 20/10* | (2016.01) | |

(52) U.S. Cl.
CPC .............. *A23P 10/30* (2016.08); *A23D 9/007* (2013.01); *A23D 9/04* (2013.01); *A23G 3/54* (2013.01); *A23L 27/50* (2016.08); *A23L 27/60* (2016.08); *A23L 27/72* (2016.08); *A23L 29/256* (2016.08); *A23P 20/105* (2016.08); *A61K 9/1682* (2013.01)

(58) Field of Classification Search
CPC ................. A23P 10/30; A23L 27/72
See application file for complete search history.

(56) References Cited

U.S. PATENT DOCUMENTS

| | | | | |
|---|---|---|---|---|
| 4,702,921 A | 10/1987 | Ueda | | |
| 2009/0291168 A1* | 11/2009 | Mangos | ................... | A23G 4/20 |
| | | | | 426/89 |

FOREIGN PATENT DOCUMENTS

| | | | | |
|---|---|---|---|---|
| EP | 0 116 311 A1 | 8/1984 | | |
| EP | 2 289 494 A1 | 3/2011 | | |
| EP | 2289494 A1 * | 3/2011 | ........... | A61K 9/4816 |
| GB | 7 627 00 A | 12/1965 | | |
| GB | 2 480 361 A | 11/2011 | | |
| GB | 2480361 A * | 11/2011 | ............. | B01J 13/22 |
| GB | 2486945 A * | 7/2012 | ........... | B01J 13/046 |
| WO | WO-2009022909 A1 * | 2/2009 | ............... | A23L 2/38 |

OTHER PUBLICATIONS

Brandau Microencapsulation in the Food Industry, Chapter 10, 2014 ,p. 109.*
What Is Sodium Alginate, http://www.visitchem.com/what-is-sodium-alginate/.*
Guo, "hydraulic Fracturing" [retrieved on Mar. 21, 2019]. Retrieved from the Internet: <URL: https://www.sciencedirect.com/topics/earth-and-planetary-sciences/emulsion>.*
My last bite, "Reverse Spherification"—Adventures in Molecular Cooking [Online], published Dec. 22, 2008, [retrieved on Oct. 8, 2019], Retrieved from the Internet: <URL: https://mylastbite.wordpress.com/2008/12/22/adventures-in-molecular-cooking-2/>.*
Whelehan, "Microencapsulation using vibrating technology", J. Microencapsul., 2011, 28(8), pp. 669-688.*
Brandau, T., Chapter 10: Annular Jet-Based Processes, Microencapsulation in the Food Industry: A Practical Implementation Guide, Elsevier Science, XP055271852, ISBN: 978-0-12-404735-8, pp. 99-110, Aug. 1, 2014.
Spanish Search Report, dated Jul. 10, 2015, in ES Application No. 201530738.
International Search Report & Written Opinion, dated May 20, 2016, in International Application No. PCT/ES2016/070160.
"Reverse Spherification"—Adventures in Molecular Cooking [2]; Accessible on the World Wide Web at https://mylastbite.wordpress.com/2008/12/22/adventures-in-molecular-cooking-2/; Dec. 22, 2008.
Office Action, dated Jun. 17, 2019, in Japanese Patent Application No. 2018-513915.
Jain, S.S., Flow-induced breakup of drops and bubbles, 2017; Downloaded from URL: https://arxiv.org/abs/1701.06157.

* cited by examiner

*Primary Examiner* — Nikki H. Dees
*Assistant Examiner* — Changqing Li
(74) *Attorney, Agent, or Firm* — Knobbe, Martens, Olson & Bear LLP

(57) ABSTRACT

Capsules are coated with a calcium alginate film, which contain two mutually immiscible or partly miscible phases, such as an aqueous phase and a hydrophobic phase or a liquid phase and a solid phase, for example. The two phases can be encapsulated and kept stable within the formed capsule.

5 Claims, No Drawings

CAPSULES CONTAINING TWO PHASES AND METHOD FOR THEIR PREPARATION

PRIORITY AND CROSS REFERENCE TO RELATED APPLICATIONS

This application is the U.S. National Stage Application under 35 U.S.C. § 371 of International Application No. PCT/ES2016/070160, filed Mar. 14, 2016, designating the U.S. and published as WO 2016/189171 A1 on Dec. 1, 2016, which claims the benefit of Spanish Patent Application No. P 201530738, filed May 27, 2015. Any and all applications for which a foreign or a domestic priority is claimed is/are identified in the Application Data Sheet filed herewith and is/are hereby incorporated by reference in their entirety under 37 C.F.R. § 1.57.

FIELD

The present invention refers to capsules coated with a calcium alginate film which contain two mutually immiscible or partly miscible phases, such as an aqueous phase and a hydrophobic phase or a liquid phase and a solid phase, for example. Moreover, the present invention also refers to the method by which said two phases can be encapsulated and kept stable within the formed capsule.

SUMMARY

The inventor of the present invention is not aware of the existence of capsules coated with calcium alginate which have two mutually immiscible or partly miscible phases in the interior thereof.

DETAILED DESCRIPTION

The biphasic capsules of the present invention can be obtained by a method usually known as "spherification", either by direct or reverse spherification.

In industrial-scale direct spherification, for example, the substance to be encapsulated and a non-calcium alginate are pumped through two concentric tubes with flow volumes that allow a drop of the substance to be encapsulated to be formed covered by a film of non-calcium alginate solution, which acts as a gelling agent. It is also possible to mix the alginate with the substance to be encapsulated. Said drop falls into a bath containing a source of calcium ions, forming a layer of gel which contains the material to be encapsulated. Said film is formed almost instantaneously on the outside and is semi-solid and gelatinous, while holding the encapsulated substance inside, in solid form if the calcium ions can migrate and in liquid form if the calcium ions cannot migrate.

An industrial spherification method is disclosed in patent application PCT WO 2009/109681 A1, for example, in which food products such as fruit pulp are encapsulated, said food products for encapsulation always being aqueous based, in other words, the substance to be encapsulated is hydrophilic.

However, in reverse spherification, the substance to be encapsulated is mixed with a source of calcium ions or magnesium ions, for example calcium chloride or other calcium salt. Next, a drop or other shape is formed with said mixture of the substance to be encapsulated and calcium ions or magnesium ions, and is introduced in a solution containing a non-calcium alginate, such as sodium alginate, for example. When the drop formed containing calcium ions is put in contact with the solution containing the alginate, a semi-solid, calcium alginate gelatinous film forms almost instantaneously, which holds within it the substance to be encapsulated.

Following exhaustive research, the inventor of the present invention has developed a spherification method by which capsules containing two substances which form two mutually immiscible or partly miscible phases can be obtained on an industrial scale, and which surprisingly are spherical shaped and, in addition, it is possible for the diameter of said capsules to be up to 50 mm without affecting the sphericity thereof, preferably within a range from 5 mm to 50 mm, more preferably from 10 mm to 50 mm, yet more preferably from 15 mm to 50 mm, from 20 mm to 50 mm, from 25 mm to 50 mm and most preferably from 30 mm to 50 mm.

The method according to the present invention is based on the use of two concentric tubes which form the two-phase drop to be encapsulated and the gelling solution, it being necessary that the substance applied through the outer tube should comprise a source of calcium ions or magnesium ions. The production of the biphasic capsules takes place using a method known as reverse spherification with some variations.

The present invention therefore discloses a method for producing capsules of biphasic substances, characterised in that it comprises the following steps:
   a) preparation of the aqueous non-calcium alginate solution in which the concentration of alginate is within the range 0.05% to 5% by weight of the solution;
   b) preparation of the substances that will form the two phases to be encapsulated in which one of said substances comprises a source of calcium ions or magnesium ions;
   c) application of the substances that will form the two phases to be encapsulated through concentric tubes, it being necessary to apply the substance that comprises the source of calcium ions or magnesium ions through the outer tube;
   d) introduction of the drop or drops formed in step (c) into an aqueous solution that contains alginate, in which the outer layer of the drop reacts forming at least one sphere which contains both phases;
   e) washing, draining and packing of the capsules formed in step (d).

The method of the present invention can be used both in the food industry and in the cosmetic, intraceutical, chemical or pharmaceutical industries, or any other industry that requires this type of capsule.

Moreover, the method of the present invention allows biphasic spheres to be obtained but clearly a person skilled in the art would be able to carry out said two-phase sphere encapsulation by other known methods, such as direct spherification or other variants of reverse spherification.

In the present invention, biphasic substances are understood to be two substances that are mutually immiscible or partly miscible. They may be organic or inorganic substances provided they comply with the above.

In addition, the term biphasic is understood in the present document to refer to two phases that are mutually immiscible or partly miscible, and may contain both two liquid phases, a liquid-solid phase where the solid can be obtained with or without a reaction, a liquid-gas phase, and in addition a person skilled in the art could use additives to emulsify the encapsulated solutions and obtain biphasic spheres that are more stable over time. Finally, biphasic spheres obtained by freezing one of the two phases and a subsequent direct or reverse spherification reaction, by means of a method known as frozen spherification are also within the scope of the present invention. Also within the scope of protection are two phases which are separated by a film of alginate, or even an alginate sphere formed earlier and incorporated with the sphere that will be formed subsequently by the method of the present invention. For example, a sphere of oil obtained by direct spherification can be included in a solution of vinegar with a source of calcium, which after contact with the alginate creates a sphere surrounded by a film of alginate which has within it said sphere of oil. It may also include a solid phase of a frozen or gelled product which is incorporated in said calcium-rich solution for subsequent gelling.

In the cosmetic industry, liquid paraffins or paraffin waxes, petroleum jellies, plant oils, waxes, fatty alcohols and their esters, lanolin and silicon and mixtures thereof can be used as the oleous phase.

In the food industry, biphasic spheres can be obtained such as vinegar-oil, soy sauce-sesame oil, mustard-olive oil, honey-olive oil and coffee-chocolate, among others. A person skilled in the art will understand that any combination of substances that form two mutually immiscible or partly miscible phases can be used for encapsulation according to the method of the present invention.

Moreover, said mutually immiscible or partly miscible substances can be mixed with seasonings, perfumes, flavourings and other oil-soluble additives.

It is clear to a person skilled in the art that the aqueous solution containing calcium ions used in the method of the present invention could be any source of calcium ions, provided it can form a calcium alginate gel which forms the outer film of the capsule. Among said sources of calcium ions can be mentioned calcium chloride, calcium lactate, calcium gluconate, for example, or a mixture thereof. Preferably, the source of calcium ions is calcium chloride.

Furthermore, said solution of calcium ions may contain any type of additive or may be mixed with any raw material that allows the organoleptic characteristics of the capsule obtained to be modified.

The alginate solution of the method of the present invention may be any non-calcium alginate salt, provided it reacts in the presence of calcium ions and forms the outer film of calcium alginate of the capsules. Preferably, the alginate used is sodium alginate. The pH of the alginate solution is between 2 and 14.

An additional advantage of the method of the present invention is that all the steps are carried out at ambient temperature. An increase or reduction in temperature, as well as increasing the production cost of the capsules, may affect the viscosity, density and surface tension of the oleous and aqueous phases present in the method, and it would therefore be necessary to modify various process parameters to obtain the same results as at ambient temperature.

EXAMPLES

Example 1

Production of Biphasic Vinegar-Olive Oil Capsules According to the Method of the Present Invention.

Commercial vinegar was taken, and 1.2% by weight of xanthan gum and 3% by weight of calcium lactate were added. A solution of sodium alginate 0.4% by weight was also prepared. Extra virgin olive oil was used for the second phase.

Drops were produced through two concentric tubes, and said drops containing olive oil in the inside tube and the prepared vinegar solution in the outer tube were introduced into a bath of the sodium alginate solution at ambient temperature. Said drops were collected and placed in a bath of water for washing. They were drained and packed. At least one capsule 45 mm in diameter was obtained, which contained two phases of olive oil and vinegar.

Example 2

Production of Biphasic Capsules of Soya-Sesame Oil.

Commercial soy sauce was taken, and 1% by weight of xanthan gum and 1% by weight of calcium chloride were added. A solution of sodium alginate 0.5% by weight was also prepared. Sesame oil was used for the second phase.

Drops were produced through two concentric tubes, and said drops containing sesame oil in the inside tube and the prepared soy sauce solution in the outer tube were introduced into a bath of the sodium alginate solution at ambient temperature. Said drops were collected and placed in a bath of water for washing. They were drained and packed. Capsules 22 mm in diameter were obtained, which contained two phases of sesame oil and soy sauce.

Example 3

Preparation of Biphasic Capsules of Jojoba Oil and Caffeine.

A 0.2% by weight caffeine solution, and 0.8% by weight of calcium chloride was added. A solution of sodium alginate 0.9% by weight was also prepared. Jojoba oil containing vitamin E at 0.5% by weight was used for the second phase.

Drops were produced through two concentric tubes, and said drops containing jojoba oil and vitamin E in the inside tube and the prepared caffeine solution in the outer tube were introduced into a bath of the sodium alginate solution at ambient temperature. Said drops were collected and placed in a bath of water for washing. They were drained and packed. At least one capsule 16 mm in diameter was obtained, which contained two phases of jojoba oil with vitamin E and caffeine.

Example 4

Preparation of Solid-Liquid Biphasic Capsules

A solution containing coffee and 1% by weight of xanthan gum was prepared and 0.2% by weight of calcium chloride was added. Liquid chocolate was also prepared and sodium alginate 0.2% by weight was added.

Drops were produced through two concentric tubes, and said drops containing the liquid chocolate solution in the inside tube and the prepared coffee solution in the outer tube were introduced into a bath of the 0.3% sodium alginate solution at ambient temperature. In said bath, the outer layer of the coffee solution reacted with the alginate forming a film of calcium alginate on the outside. In turn, the calcium included in the coffee reacted with the sodium alginate included in the chocolate, forming an outer film on the chocolate. This chocolate solidified completely, and at least one capsule 10 mm in diameter was obtained, which contained two phases: a solid chocolate phase and a liquid coffee phase.

Example 5

Production of Biphasic Capsules of Vinegar-Olive Oil Macerated with Rosemary

Commercial vinegar was taken, and 1% by weight of xanthan gum and 0.4% by weight of calcium lactate were added. In addition, olive oil macerated with rosemary was taken for the second phase.

Drops were produced through two concentric tubes, and said drops containing olive oil macerated with rosemary in the inside tube and the prepared vinegar solution in the outer tube were introduced into a bath of 0.3% sodium alginate solution at ambient temperature. Said drops were collected and placed in a bath of water for washing. They were drained and packed. At least one capsule 28 mm in diameter was obtained, which contained two phases of olive oil macerated with rosemary and vinegar.

Although the invention has been described with respect to preferred embodiments, these should not be considered as limiting the invention, which will be defined by the widest interpretation of the following claims.

The invention claimed is:

1. A method for producing biphasic spherical capsules comprising at an outer portion thereof a film of calcium alginate and comprising in their interior two liquid substances each of said substances forming a separate continuous phase wherein the method comprises:
   (a) preparing an aqueous non-calcium alginate solution in which the concentration of alginate is within the range 0.05% to 5% by weight of the solution;
   (b) preparing the two liquid substances that will form the separate continuous phases in which one of said substances comprises a source of calcium ions or magnesium ions;
   (c) applying the substance that comprises the source of calcium ions or magnesium ions through an outer tube, and applying the other of the two liquid substances through an inner tube, wherein the outer and inner tubes are concentric to form drop or drops;
   (d) introducing the drop or drops formed in step (c) into the aqueous non-calcium alginate solution, in which the outer layer of the drop or drops reacts with the non-calcium alginate in the aqueous non-calcium alginate solution forming at least one capsule containing both phases;
   (e) collecting, washing, draining and packing the at least one capsule formed in step (d),
   wherein the method is a reverse spherification, and
   wherein the at least one capsule has a diameter in the range of 5 mm to 50 mm.

2. The method according to claim 1, wherein the source of calcium ions is selected from the group consisting of solutions of calcium chloride, calcium lactate, calcium gluconate and a mixture thereof.

3. The method according to claim 2, wherein the source of calcium ions is the solution of calcium chloride.

4. The method according to claim 1, wherein the alginate used is sodium alginate.

5. The method according to claim 1, wherein the pH of the aqueous non-calcium alginate solution is between 2 and 14.

\* \* \* \* \*